United States Patent [19]

Glahn

[11] Patent Number: 6,143,346
[45] Date of Patent: Nov. 7, 2000

[54] PECTIN PROCESS AND COMPOSITION

[75] Inventor: Poul-Egede Glahn, Skensved, Denmark

[73] Assignee: Hercules Incorporated, Wilmington, Del.

[21] Appl. No.: 08/161,635

[22] Filed: Dec. 2, 1993

[51] Int. Cl.[7] .............................. A23L 1/05; A61K 7/00; C08B 37/06
[52] U.S. Cl. ................. 426/577; 424/401; 536/2
[58] Field of Search ................ 424/401; 536/2; 426/577

[56] References Cited

U.S. PATENT DOCUMENTS

| | | | |
|---|---|---|---|
| 4,143,172 | 3/1979 | Mitchell | 426/532 |
| 4,370,354 | 1/1983 | Leipold | 426/573 |
| 4,389,426 | 6/1983 | Reismann | 426/602 |
| 4,430,349 | 2/1984 | Malone | 426/34 |
| 4,672,034 | 6/1987 | Rombouts | 536/2 |
| 4,737,582 | 4/1988 | Goldman | 536/2 |
| 4,774,095 | 9/1988 | Kleinschmidt et al. . | |
| 4,988,530 | 1/1991 | Hoersten | 426/577 |
| 5,071,970 | 12/1991 | le Grand | 536/2 |
| 5,238,699 | 8/1993 | King | 426/573 |

FOREIGN PATENT DOCUMENTS

| | | |
|---|---|---|
| 0432835A1 | 6/1991 | European Pat. Off. . |
| 0432835 | 3/1994 | European Pat. Off. ........... A23L 1/05 |
| 0432835B1 | 3/1994 | European Pat. Off. . |
| 1185280 | 8/1959 | France . |
| 2442980 | 3/1976 | Germany . |
| 1076501 | 4/1986 | Japan .......................................... 536/2 |
| 1474990 | 5/1977 | United Kingdom . |
| 8912648 | 12/1989 | WIPO . |

OTHER PUBLICATIONS pp. 4–6 of English language translation of opposition of Copenhagen Pectin to petition of P.E. Glahn for legal aid, Sep. 1996.
AN 84–187728, Derwent Publication Ltd., Week 8430.
AN 85–181395, Derwent Publication Ltd., week 8530.

*Primary Examiner*—Thurman K. Page
*Assistant Examiner*—Alysia Berman
*Attorney, Agent, or Firm*—Martin F. Sloan

[57] ABSTRACT

A process is provided for treating a solution, gel, or suspension of pectin starting material having a degree of esterification greater than about 60% with a cation-containing preparation to obtain at least a first fraction having a higher degree of calcium sensitivity and a second fraction having a lower degree of calcium sensitivity than said pectin starting material. The resultant composition has a degree of esterification greater than about 60% and a ratio of calcium sensitive pectin to the sum of calcium sensitive pectin and non-calcium sensitive pectin greater than about 0.60. Compositions using citrus pectin have a degree of esterification less than about 80% and a ratio on non-calcium sensitive pectin to the sum of calcium sensitive pectin and non-calcium sensitive pectin greater than about 0.60. These compositions are used, for example, in admixture with foodstuffs, in personal hygienic devices, and in cosmetics.

19 Claims, No Drawings

PECTIN PROCESS AND COMPOSITION

The present invention relates to pectin compositions and processes for preparing the same.

BACKGROUND OF THE INVENTION

Processes for preparation of pectins are well known, as are many uses for these products. In general, typical pectin processes include the steps of:

(1) acid extraction from plant starting material at low pH, (2) purification of the liquid extract, and (3) isolation of the extracted pectin from the liquid.

In the acid extraction step, plant material is typically treated with dilute acids such as nitric-, sulfuric-, hydrochloric- or other inorganic or organic acids to remove the pectin from the cellulose components of the material. Commonly used plant starting materials are citrus peels from juice production and apple pomace from apple juice and cider production. Other plant starting materials can also be used, such as sugar beet, before or after sugar extraction, sunflower heads after removal of the seeds, and other vegetables or waste products from plants. Extraction conditions are selected such that a major part of the pectin molecules contained in the plant starting material is transferred from the cell walls of said plant starting material to the extraction medium.

The quantity and quality of the extracted pectin depends on the raw material source and the selection and control of the extraction conditions such as pH, temperature and extraction time.

After the acid extraction step, a mixture of solid plant material and liquid that contains the pectin remains. This mixture is then subjected to a purification step In which the solid plant material la removed by filtration, centrifugation or other conventional separation steps known to those skilled in the art.

The extract can, optionally, be further purified by ion exchange and concentrated by evaporation of part of the water. Alternatively, the purification step can be carried out by reverse osmosis, concentrating and purifying the extract in the same step.

The pectin in the acid extract can be isolated by reacting with aluminum salts after adjusting the pH. The aluminum pectinate gel thus formed is treated with alcohol/acid mixture to wash out the aluminum salt and transformed the pectin into pectic acid. The pectic acid can then be neutralized and a substantial amount of the water is removed by washing with slightly alkaline alcohol.

More commonly, the pectin is isolated by treating the pectin solution with an appropriate alcohol to render the pectin insoluble in the ensuing blend of alcohol and water. Any alcohol or other organic solvent miscible with water can be used, most often ethyl alcohol, methyl alcohol or isopropyl alcohol. isopropyl alcohol is most preferred.

The insolubilized pectin is separated from the alcohol/water mixture by appropriate means such as filtration, centrifugatlon, etc. The resulting pectin cake is dried and milled to the desired particle size.

in typical commercial processes, the presence of high levels of polyvalent cation is avoided in steps (1) and (2) as described above. While low levels of cation, i.e., those materials naturally present in the starting materials, may be tolerated in some instances, it has been the general practice to never add additional cation(s) to the processes. This would result in unacceptable increases in viscosity and unacceptable levels of insoluble pectin in the final product.

Industrially produced pectins are made up primarily of polygalacturonic acid chains in which rhamnose may be found. Neutral sugars may be attached to the rhamnose units. The anhydrogalacturonic acid makes up at least 65% of the dry matter in commercial type pectins. The galacturonic acids are partly esterified with methyl alcohol.

According to convention, pectins with more than 50% of the carboxylic acid groups esterified with methyl alcohol are referred to as high methoxyl pectins; whereas, pectins with less than 50% of the carboxylic acid groups esterified with methyl alcohol are called low methoxyl pectins.

The extract as obtained by the commercial production is composed of those molecules that are soluble under the conditions of pH, temperature, and time used during the extraction. The extract is composed of a mixture of molecules which differ according to molecular weight, distribution of molecular weight, and degree of esterification.

The properties of the pectin obtained are, therefore, very much dependent on the specific mixture of molecular configurations present in the isolated pectin. This mixture of molecules can be controlled only to a certain degree by the pectin manufacturer by selection of raw materials and extraction conditions. For this reason, variation in pectin properties is seen from extract to extract, from manufacturer to manufacturer, and normalization of the properties is generally necessary. This may be accomplished by blending different extracts and diluting with acceptable diluent such as sugar, dextrose, fructose, etc.

One of the main functional variations between high methoxyl pectins is their sensitivity to the presence of varying concentration of polyvalent cations. it is known that pectins of high degree of esterification, e.g., greater than fifty, are not particularly useful for applications involving reaction of the pectin with polyvalent cations such as calcium.

SUMMARY OF INVENTION

It has unexpectedly been discovered that commercially extracted pectins contain a mixture of a calcium-sensitive fraction and a non-calcium sensitive fraction which can be separated into separate fractions in a commercially feasible manner. Calcium sensitivity is a strong indicator of sensitivity to other cations; this discovery applies to sensitivity to such other cations also.

Accordingly, the present invention relates to a process comprising treating a solution, gel, or suspension of pectin starting material having a degree of esterification greater than about 60% with a cation-containing preparation to obtain at least a first fraction having a higher degree of calcium sensitivity and a second fraction having a lower degree of calcium sensitivity than said pectin starting material.

The present invention further relates to a composition comprising pectin having a degree of esterification greater than about 60% and a ratio of calcium sensitive pectin to the sum of cation sensitive pectin (CSP) and non-calcium sensitive pectin (NCSP) greater than 0.60.

The present invention further relates to a composition comprising citrus pectin having a degree of esterification less than about 80% and a ratio of NCSP to the sum of CSP and NCSP greater than 0.60.

The present invention also relates to a composition comprising a di- or trivalent metal salt of pectin that has a water absorption property of at least about 20.

In addition, the present invention relates to a food composition comprising in admixture a foodstuff and the above described CSP and NCSP compositions.

Furthermore, the present invention relates to a personal hygienic device containing the above described compositions.

Also, the present invention relates to a cosmetic composition comprising at least one cosmetic ingredient and the above described compositions.

Not being bound by theory, it appears that the compositions described herein offer unique performance characteristics heretofore not obtained. The CSP has the ability to imbibe more water than a corresponding material of lower degree of esterification because it has a more open structure. This results in a softer, more deformable gel which is important for many applications in food, cosmetics, etc.

The gel is easily reduced to desirable small particles, and its improved deformability results in better mouth feel and creaminess.

Current commercial pectins having a degree of esterification of less than about 50% have more sites for calcium crosslinking and therefore a denser structure with less ability to absorb water. Pectins with lower degree of esterification than about 50% form firmer gels with calcium, resulting in lose palatable products.

The benefits of the present invention would readily occur to the artisan having the benefit of the present disclosure. For example, as compared to a non-separated pectin product, CSP composition according to the present invention would be more efficient in many applications, for example, up to two times more efficient in stabilizer applications for acidified protein systems. Also, for example, NCSP compositions according to the present invention provide better performance in those applications requiring pectin that is not reactive with cations. The NCSP, according to the present invention, has the advantage that it will not form gels in the presence of calcium. This attribute has advantages in many end-use applications.

DETAILED DESCRIPTION OF THE INVENTION

The present invention relates to a process comprising treating a solution, gel, or suspension of pectin starting material having a degree of esterification greater than about 60% with a cation-containing preparation to obtain at least a first fraction having a higher degree of calcium sensitivity and a second fraction having a lower degree of calcium sensitivity than said pectin starting material.

As used herein, "calcium sensitivity" is intended to mean that property of a pectin product related to an increase in the viscosity of a solution of the pectin product under appropriate conditions using the procedure as described below in the section labelled "Analytical Procedures". As already indicated above, since calcium sensitivity is a strong indicator of sensitivity to other cations, the present invention covers sensitivity to such other cations also.

As used herein, "degree of esterification" is intended to mean the extent to which free carboxylic acid groups contained in the polygalacturonic acid chain have been esterified (e.g., by methylation) or in other ways rendered non-acidic (e.g., by amidation).

As indicated, processes in accordance with the present invention comprise the treatment of pectin starting material. As used herein, "pectin starting material" is intended to mean pectin product obtained by separation of pectin from plant material. The pectin starting material could be, for example, the acid pectin extract after purification or it could be wet pectin cake obtained after treating the acid pectin solution with an alcohol. Further, the pectin starting material could be, for example, the dried or partly dried pectin in said pectin cake from precipitation, or it could be the dried, milled pectin powder as normally produced by pectin manufacturers.

The pectin starting material is treated with a cation-containing preparation. As used herein, "cation-containing preparation" is intended to mean any source of free cation. The cation is preferably a metal ion derived from salts selected from the group consisting of alkaline earth metal salts, alkali metal salts, transition metal salts, and mixtures thereof, provided that such salts are reasonably soluble in the solvent, e.g., water or water/alcohol mixtures. When a metal ion is used as the cation, it is preferably selected from the group consisting of calcium, iron, magnesium, zinc, potassium, sodium, aluminum, manganese, and mixtures thereof. More preferably, the metal cations are selected from the group consisting of calcium, iron, zinc, and magnesium. Most preferably, the cation is calcium. Mixtures of two or more metal cations may be employed. However, if a monovalent metal cation is employed, a di- or trivalent metal cation, such as calcium, must also by present. Preferably, when such mixtures are used, one of the metal cations is calcium.

Examples of metal salts that can be used in the practice of the present invention, provided they are reasonably soluble in the solvent, include, but are not limited to, calcium acetate, calcium acid phosphate, calcium carbonate, calcium chloride, calcium citrate, calcium dihydrogen phosphate, calcium formate, calcium gluconate, calcium glutamate, calcium glycerate, calcium glycerophosphate, calcium glycinate, calcium hydrogen phosphate, calcium hydroxide, calcium iodide, calcium lactate, calcium lactophosphate, calcium magnesium carbonate, calcium magnesium inositol hexaphosphate, calcium phosphate tribasic, calcium-o-phosphate, calcium proplonate, calcium pyrophosphate, calcium succinate, calcium sucrate, calcium sulfite, calcium tetraphosphate, iron (II) acetate, iron (III) acetate, iron (III) acetate hydroxide, iron (III) ammonium chloride, iron (III) ammonium citrate, iron (II) ammonium sulfate, iron (II) carbonate, iron (II) chloride, iron (III) chloride, iron choline citrat, iron (II) citrate, iron dextran, iron (II) formate, iron (III) formate, iron (III) hypophosphite, iron (II) lactate, iron (II) acetate, iron (II) phosphate, iron (III) potassium oxalate, iron (III) pyrophosphate, iron (III) sodium citrate, iron (III) sodium pyrophosphate, iron(II) sulfate, iron (III) sulfate, magnesium ammonium phosphate, magnesium ammonium sulfate, magnesium carbonate, magnesium chloride, magnesium citrate, magnesium dihydrogen phosphate, magnesium formate, magnesium hydrogen phosphate, magnesium hydrogen-o-phosphate, magnesium hydroxide, magnesium hydroxide carbonate, magnesium lactate, magnesium nitrate, magnesium oxalate, magnesium oxide, magnesium phosphate, magnesium proplonate, magnesium pyrophosphate, magnesium sulfate, zinc acetate, zinc ammonium sulfate, zinc carbonate, zinc chloride, zinc citrate, zinc formate, zinc hydrogen phosphate, zinc hydroxide, zinc lactate, zinc nitrate, zinc oxide, zinc phosphate, zinc phosphate monobasic, zinc phosphate tribasic, zinc-o-phosphate, zinc propionate, zinc pyrophosphate, zinc sulfate, zinc tartrate, zinc valerate, and zinc-iso-valerate.

The preferred salts are calcium salts such as calcium chloride, calcium hydroxide, calcium acetate, calcium proplonate, calcium oxide, calcium gluconate, calcium lactate, and calcium carbonate. The most preferred calcium salt is calcium chloride.

In processes in accordance with the present invention, the cation-containing preparation preferably contains a di- or trivalent cation, and optionally at least one water miscible solvent. Under appropriate conditions, the polyvalent cation forms an insoluble cation pectinate salt or gel. n has unexpectedly been found that a portion of the pectin does not form such an insoluble salt with said polyvalent cations, but diffuses out of salad gel into the salt solution forming a separate pectin phase in said solution. The pectin can, accordingly, be separated into two or more fractions, one containing pectin that has reacted with the cation forming a gel matrix insoluble in the solvent. A second fraction, which does not form such a gel matrix, is transferred to the liquid phase until equilibrium is reached between the liquid phase and the liquid within the gel particles containing the matrix-forming pectinate.

The preferred cation is calcium ion in aqueous solution, optionally mixed with a solvent such as methyl alcohol, ethyl alcohol, propyl alcohol, isopropyl alcohol, acetone, ethyl acetate, and any other organic solvent that is miscible with water. When mixed with alcohol, care should be exercised to avoid alcohol levels that will result in precipitation of an insoluble pectin compound. The preferred solution is a mixture of alcohol and water. Most preferred is a mixture of isopropyl alcohol and water.

The cation concentration can be varied over a wide range, with the upper limit being determined only by economic and practical considerations. It is preferred that the upper limit be about 60 millimoles cation per liter of reaction medium (60 mM). What is meant by reaction medium is what results from reacting the pectin starting material with the cation-containing preparation.

A more preferred upper limit is about 45 mM cation. The lower limit is determined by that amount of cation that would provide the desired degree of separation into the at least first and second fractions. The preferred lower limit is about 5 mM cation. A more preferred lower limit is about 10 mM cation, with about 30 mM being the most preferred lower limit.

The pH of the reaction medium influences the matrix-forming ability of the pectin starting material. If the pH is too low, no matrix is formed. It is believed that the pH should be at least about 2. The lower limit is preferably at least about 3, with about 4 being the most preferred. The upper limit of the pH is only determined by the stability of the pectin starting material under the combination of pH, temperature, and time being used. It is believed that the upper limit should be about 8. The preferred upper limit should be about 6, with about 5 being the most preferred upper limit.

As indicated above, processes in accordance with the present invention comprise treating pectin starting material having a degree of esterification of greater than about 60% to obtain at least a first fraction having a higher degree of calcium sensitivity and a second fraction having a lower degree of calcium sensitivity than the pectin starting material. It is preferred that the first fraction has a degree of esterification of at least 1% lower than the degree of esterification of the starting material, more preferred at least 3% lower and most preferred at least 5% lower than the degree of esterification of the starting material. The second fraction accordingly has a preferred degree of esterification of at least 1% higher than the degree of esterification of the starting material, more preferred a degree of esterification of at least 3% higher, and most preferred at least 7% higher than the degree of esterification of the starting material.

The separation of the at least first and second fractions in accordance with the present invention is preferably performed as a separation into a gel phase and a liquid phase, respectively. The gel phase is predominantly the reaction product of the cation in the cation-containing preparation and the calcium-sensitive fraction present in the pectin starting material. The liquid phase is predominantly the pectin fraction in the starting material that does not form a gel with the cation-containing preparation. Various techniques conventional in the art could be used to perform the separation step. Preferably, the separation is performed by filtration using a washing solution to complete the separation. The composition of the preferred washing solution is comprised of the same cation-containing preparation used to treat the pectin starting material.

After the washing steps, the first fraction has a calcium sensitivity (CS) of at least 10% higher than the calcium sensitivity of the starting material. The CS of the first fraction preferably is at least 25% higher than the starting material, more preferably at least 50% higher than the starting material, and most preferably at least 100% higher than the starting material.

In a preferred embodiment of the present invention, the purified pectin extract is reacted with a solution of a cation salt under substantially non-shear flow conditions, forming large gel particles visible to the naked eye. The gel particles can then be separated in any appropriate way from the liquid and resuspended in fresh liquid or liquid containing a lower concentration of the NCSP.

The gel fraction can be converted into its acid form or a salt of a monovalent metal or of ammonia by treating the alcohol precipitated fractions with an acid alcohol solution washing out the polyvalent metals. The fractions may then be partly or completely neutralized by washing with an alcohol solution of the desired salt.

Alternatively, the fractions may be acidified before the alcoholic precipitation and subsequently washed with acid alcohol. Further, the fractions may be treated with an ion exchange resin carrying the desired monovalent cation and subsequently precipitated with alcohol. The preferred method depends on the further use of the fractions. The fractions treated in this way may be worked up as described above.

At least one of the separated gel and liquid fractions may then be dehydrated, dried and milled. Preferably, both fractions are dehydrated, dried and milled. The dehydration is performed to remove the bulk of the water before the drying step. While any known technique could be used for dehydration, preferably the fractions are treated with alcohol. The water/alcohol phase formed in the dehydration is substantially removed by decantation, centrifugation or filtration using any conventional technique. Drying is accomplished by conventional techniques, e.g., atmospheric or reduced-pressure ovens, to a moisture content of less than 50%, preferably less than 25%. The drying temperature should be maintained below the temperature at which the pectin starts to lose its properties, e.g., color, molecular weight, etc. Milling techniques are well-known and any known technique can be used to mill the pectin product to the desired particle size. It is most preferred that the final product be in dry, powder form, with a moisture content of 12% or less. Dry, powder form is intended to mean that the product be pourable without substantial caking. This is preferred for ease of use.

Processes in accordance with the present invention could be either continuous or batch, with continuous being preferred.

The ratio of calcium sensitive pectin (CSP) to the sum of CSP and non-calcium sensitive pectin (NCSP) is hereinafter referred to as Calcium Sensitive Pectin Ratio (CSPR). As indicated above, pectin compositions in accordance with the present invention have a CSPR greater than about 0.60. The preferred compositions have a CSPR of at least 0.65. A more preferred CSPR is 0.75 with 0.85 being most preferred.

The degree of esterification of pectin starting material in accordance with the present invention is greater than about 60%. The degree of esterification is preferably at least 65%. The most preferred degree of esterification (degree of esterification) is at least 70%.

As indicated above, the pectin can be obtained from various sources such as citrus peels from juice production, apple pomace from apple juice and cider production, sugar beet, sunflower heads, and other vegetables or waste products from plants. The preferred pectins are citrus pectins. These pectins are preferably selected from the group consisting of lime, lemon, grapefruit, and orange.

Compositions in accordance with the present invention further comprises a di- or trivalent metal salt of pectin that has a water absorption property of at least about 20. The metal salts are preferably the same as those described above in defining compositions in accordance with the present invention. The preferred pectins are also the same as those described above in defining compositions in accordance with the present invention.

"Water absorption property" is understood to mean the ability of the pectin sample to take up water when immersed in distilled water or a 1% NaCl solution made with distilled water.

Also in accordance with the present invention, a food composition comprises in admixture a foodstuff and the pectin composition s described above, As used herein, foodstuff is intended to mean any food, food composition, food ingredient, or food product, whether comprised of a single ingredient or a mixture of two or more ingredients, whether liquid, liquid containing, or solid, whether primarily carbohydrate, fat, protein, or any mixture thereof, whether edible per se or requiring preliminary conventional steps like cooking, mixing, cooling, mechanical treatment, and the like.

The invention is particularly applicable to meat, poultry, fish products, dairy products such as milk, ice cream, yoghurt, cheese, pudding, and flavored dairy drinks, baked foods such as bread, cake, cookies, crackers, biscuits, pies, donuts, pretzels, and potato chips, non-dairy spreads, mayonnaise, soups, sauces, dips, dressings, frozen confections, fruit preparations, jams and jellies, beverages, water gels, confectionery jelly, and low fat spreads.

Further, in accordance with the present invention, a personal hygienic device contains the pectin compositions as described above. The invention is particularly applicable to tampons, incontinent devices, disposable diapers, and wound dressings.

Additionally, in accordance with the present invention, a cosmetic composition comprises at least one cosmetic ingredient and the pectin compositions as described above. The composition is especially applicable to sun tan lotions, sun screen compositions, creams which include emollients such as isopropylmyristate, silicone oils, mineral oils, and vegetable oils which give rise to a tactile response in the form of an increase in skin lubricity, and skin coolants such as menthol, menthyl lactate, menthyl pyrrolidone carboxylate N-ethyl-p-menthane-3-carboxamide and other derivatives of menthol, all of which give rise to a tactile response in the form of a cooling sensation on the skin, perfumes, deodorants other than perfumes, whose function is to reduce the level of, or eliminate microflora at the skin surface, especially those responsibie for the development of body odor, antiperspirant actives, whose function is to reduce or eliminate the appearance of perspiration at the skin surface, and anticholinergic actives, whose function is to reduce or eliminate the generation of perspiration before it reaches the skin surface.

An additional composition in accordance with the present invention comprises a citrus pectin having a degree of esterification less than about 80% and a ratio of non-calcium sensitive pectin to the sum of calcium aensitive pectin and non-calcium sensitive pectin greater than 0.60 (preferably greater than 0.70, more preferably greater than 0.80, and most preferred being greater than 0.90). While the upper limit for degree of esterification is indicated to be less than 80%, it could be less than about 75%, or less than 70%, or even less than 65%. The lower limit for degree of esterification is limited only by the final product retaining its non-calcium sensitivity. it is believed that the degree of esterification could be as low as 45%. However, the lower limit could be 50%. This composition may be aminated (e.g., by adding up to 25% amide groups). Such compositions are particularly useful in foodstuff such as lame and jellies, beverages, water gels, confectionery jelly, and low fat spreads.

Analytical Procedures

Determination of Calcium Sensitivity (CS) of Pectin Samples

A pectin solution of desired concentration is prepared in distilled water and pH adjusted to 1.5 with 1 M HCl. The pectin sample must be in acid or monovalent salt forms. The concentration used in Examples 1 and 2 is 0.60%.

145 g portions of this pectin solution are measured into viscosity glasses.

5 ml of a solution containing 250 mM calcium chloride is added to the 145 g pectin solution to give a final concentration of 8.3 mM calcium.

With efficient stirring with a magnetic stirrer 25 ml of an acetate buffer containing 1 M of acetate ion s and a pH of 4.75 is added to the pectin solution to bring pH to 4.2.

The magnet is taken out, and the glass is left at room temperature (25° C.) until the next day, when the viscosity is measured at 25° C. with a Brookfield viscometer.

While the method is most suitable for pectin samples having a viscosity not higher than 100, viscosity up to 200 Brookfied units can be measured with good reproducibility. Pectin samples with higher viscosity tend to gelify, resulting in less reproducible results. The method, however, gives a fair indication of the relative calcium sensitivity of samples.

When the viscosity of the same pectin samples is measured without the addition of calcium chloride—diluting with distilled water instead, the contribution by the calcium ions to the viscosity of the calcium containing solution can be calculated by subtracting the value for the calcium free solution from the value for the calcium containing solution. For pectin samples with very low calcium sensitivity (CS), this difference is a few units or nil.

The results reported in the examples are the difference between measured viscosity with and without the addition of calcium.

Determination of Ratio of Calcium Sensitive Pectin and Non Calcium Sensitive Pectin in a Pectin Sample 1000 g pectin sample is dissolved in 50 kg demineralized water by heating to 70° C. The solution is cooled to approximately 20° C.

If the sample contains sugar or other ingredients, the weight is corrected accordingly.

Samples with more than approximately 5 mg Ca or other di- or trivalent cations per gram pectin are either acid-washed to remove these cations, or the solution is ion exchanged to obtain the salt of a monovalent cation.

The pH of the solution is adjusted to 4.0.

The exact amount of pectin in the solution is determined by mixing 2.5 kg of the solution with 5.0 liters of 80% isopropyl alcohol to precipitate the pectin. The precipitate is collected on a nylon cloth, washed twice with 60% isopropyl alcohol, dried at 60° C. over night and weighed. The pectin concentration in the pectin solution is calculated by dividing the weight of dried pectin by the weight of pectin solution precipitated with isopropyl alcohol, designated A g pectin per kg solution.

A portion of the solution, in the range 30–35 kg, is weighed out to the second decimal and mixed under gentle stirring with an equal amount of a solution containing:

38.7 kg demineralized water
9.9 kg 80% lsopropyl alcohol (IPA)
0.66 kg $CaCl_2$, 6 $H_2O$ After mixing of the two solutions, this results in a Ca-content of 30 mM and 8% (100%) IPA.

The suspension of gel particles formed is left for 24 hours with occasional stirring.

The gel particles are separated from the liquid phase and washed twice in equal amounts of a solution containing 30 mM Ca and 8% IPA (100%). The equilibration time is 24 hours for each washing.

The total amount of washed gel phase is weighed.

The pectin concentration in the gel phase is determined by mixing 15–20 kg of gel phase, weighed out to the second decimal, with twice its value of 80% IPA, washed twice in 60% IPA, dried and weighed. The pectin concentration in the gel phase is calculated by dividing the weight of dried pectin by the weight of the gel phase, designated as B g pectin per kg gel phase.

The ratio of CSP is calculated according to the formula:

$$CSPR = \frac{\text{weight of gel phase} \times B}{\text{weight of pectin solution} \times A}$$

The ratio of NCSP is found by subtracting the ratio of CSP from 1.

Water Absorption Test

Weigh out 0.20 g sample. Add sample to a 2"×3" tea bag. Immerse the tea bag in 50 grams of a 1% NaCl solution for 10 minutes. Drain tea bag and weigh.

Water absorption is calculated by the following equation:

$$\frac{W_w - W_b - W_s}{W_s} = - \text{ g absorbed water per g sample}$$

$W_w$ – weight of wet tea bag $W_b$ – weight of empty tea bag blank $W_s$ – weight of sample Galacturonic Acid
Degree of Amidation
Degree of Substitution Weigh 5 g of the sample to the nearest 0.1 mg and transfer to a suitable beaker. Stir for 10 minutes with a mixture of 5 ml of hydrochloric acid TS and 100 ml of 60% ethanol. Transfer to a fitted glass filter tube (30 to 60 ml capacity) and wash with six 15 ml portions of the HCl-60% ethanol mixture, followed by 60% ethanol until the filtrate is free of chlorides. Finally wash with 20 ml of ethanol, dry for 2.5 hours in an oven at 105° C., cool and weigh. Transfer exactly one-tenth of the total net weight of the dried sample (representing 0.5 g of the original unwashed sample) to a 250 ml conical flask and moisten the sample with 2 ml of ethanol TS. Add 100 ml of recently boiled and cooled distilled water stopper and swirl occasionally until a complete solution is formed. Add 5 drops of phenolphthalein TS, titrate with 0.1 N sodium hydroxide TS and record the results as the initial title ($V_1$).

Add exactly 20 ml of 0.5 N sodium hydroxide TS, stopper, shake vigorously and let stand for 15 minutes. Add exactly 20 ml of 0.5 N hydrochloric acid TS and shake until the pink color disappears. After adding three drops of phenolphthaleln TS, titrate with 0.1 N sodium hydroxide TS to a faint pink color which persists after vigorous shaking; record this value as the saponification title ($V_2$).

Quantitatively transfer the contents of the conical flask into a 500-ml distillation flask fitted with a Kleldahl trap and a water-cooled condenser, the delivery tube of which extends well beneath the surface of a mixture of 150 ml of carbon dioxide-free water and 20.0 ml of 0.1 N hydrochloric acid TS in a receiving flask. To the distillation flask add 20 ml of a 1-in-10 sodium hydroxide solution, seal the connections, and then begin heating carefully to avoid excessive foaming. Continue heating until 80–120 ml of distillate has been collected. Add a few drops of methyl red TS to the receiving flask, and titrate the excess acid with 0.1 N sodium hydroxide TS, recording the volume required, in ml, as S. Perform a blank determination on 20.0 ml of 0.1 N hydrochloric acid TS, and record the volume required, in ml, as B. Record the amide title (B-S) as $V_3$.

Calculate degree of estorification (as % of total carboxyl groups) by the formula:

$$100 \times \frac{V_2}{V_1 + V_2 + V_3}$$

Calculate degree of amidation (as % of total carboxyl groups) by the formula:

$$100 \times \frac{V_3}{V_1 + V_2 + V_3}$$

And calculate mg of galacturonic acid by the formula:

$$19.41 \times (V_1 + V_2 + V_3)$$

The mg of galacturonic acid obtained in this way is the content of one-tenth of the weight of the washed and dried sample. To calculate % galacturonic acid on a moisture-and-ash-free basis, multiply the number of mg obtained by 1000/x, x being the weight in mg of the washed and dried sample.

EXAMPLES

Example 1

12.5 g milled, dry high methoxyl pectin was dispersed in 1 liter of a solution containing:

| | |
|---|---|
| Isopropyl alcohol, 8.0% | 150 ml |
| Distilled water | 750 ml |
| CaCl$_2$, 2H$_2$O | 4.4 g |

This dispersion was stirred gently and its pH was adjusted in the range of 3.6 to 4.0 with sodium carbonate. The reaction mass was separated on a nylon cloth into a liquid and a gelled fraction. The cake was washed by resuspending the cake into 1 liter of the above solution. The insoluble material was separated from the liquid on a nylon cloth after stirring for 1 hour. The washing was repeated twice.

The solid phase was dried by mixing with isopropyl alcohol, separating the alcohol/water phase from the pectin and drying the pectin material. The combined washing solutions were concentrated by evaporation and the pectin isolated by mixing the concentrated extract with isopropyl alcohol and proceeding as for the gel phase.

Nearly equal amounts of the two fractions were obtained with the following representative analytical data:

| | Gel | Liquid |
|---|---|---|
| degree of esterification % | 66 | 74 |
| AA %[1] | 86 | 85 |
| CS[2] | 930 | 0.3 |

[1] AA means anhydrogalacturonic acid.
[2] CS means calcium sensitivity.

The starting material has a degree of esterification of 71% and a CS of 300.

Example 2

1000 g pure pectin was dissolved in 50 kg demineralized water by heating to 70° C. and cooled to approximately 20° C.

The pure pectin contained less than approximately 5 mg calcium or other di- or trivalent cations per gram pectin.

The pH of the solution was adjusted to 4.0.

The solution was mixed under gentle stirring with an equal amount of a solution containing:

38.7 kg demineralized water 9.9 kg isopropyl alcohol (IPA)

0.66 kg CaCl$_2$. 6 H$_2$O

After mixing the two solutions, the resultant gel suspension contained a Ca-content of 30 mM and an isopropyl alcohol (IPA) content of about 8%.

The suspension of gel particles formed was left for 2 hours with occasional stirring.

The gel particles were separated from the liquid phase and washed twice in equal amounts of a solution containing 30 mM Ca and 8% IPA. The equilibration time was 2 hours.

The gel phase was dehydrated by mixing with twice its weight of 80% IPA, washed twice in 60% IPA, dried and weighed.

| | Starting Material | CSP Fraction | NCSP Fraction |
|---|---|---|---|
| degree of esterification % | 71.5 | 67.5 | 78.5 |
| AA % | 83.1 | 87.3 | 86.4 |
| CS | 360 | 850 | 0.1 |
| % of Fractions | 100 | 61 | |

The average % degree of esterification based on the amount of the two fractions and their % degree of esterification is calculated to 71.8, in good accordance with the value measured on the starting material.

The degree of esterification value of the CSP fraction is decreased by (71.5−67.5)/71.5 100=5.6% as compared to the starting material. The degree of esterification value of the NCSP fraction is increased by (78.5−71.5)/71.5 100=9.8% as compared to the starting material.

Example 3

The separation was carried out as described in Example 2 except that only 6% IPA was used on a pectin with a % degree of esterification of 60.4.

| | Starting Material | CSP Fraction | NCSP Fraction |
|---|---|---|---|
| degree of esterification % | 60.4 | 54.3 | 67.0 |
| AA % | 84.4 | 85.7 | 84.7 |
| CS | 3.6 | 45 | 0.5 |
| % of Fractions | 100 | 55 | 45 |

The average % degree of esterification based on the amount of the two fractions and their % degree of esterification is calculated to 60.0 in good accordance with the value measured on the starting material.

Example 4

The separation was carried out as described in Example 2 except that 12% IPA was used on a pectin with a % degree of esterification of 68.3.

| | Starting Material | CSP Fraction | NCSP Fraction |
|---|---|---|---|
| degree of esterification % | 68.3 | 64.8 | 76.6 |
| AA % | 83.0 | 89 | 88.4 |
| SS | 4.9 | 109 | 0 |
| % of Fractions | 100 | 57 | 43 |

The average % degree of esterification based on the amount of the two fractions and their % degree of esterification is calculated to 69.8 in reasonably good accordance with the value measured on the starting material.

Example 5

The separation was carried out as described in Example 2 on a pectin with a % degree of esterification of 71.9.

|  | Starting Material | CSP Fraction | NCSP Fraction |
|---|---|---|---|
| degree of esterification % | 71.9 | 65.6 | 77.3 |
| AA % | 80.9 | 84.7 | 83.4 |
| CS | 87 | 1080 | 0.4 |
| % of Fractions | 100 | 42 | 58 |

The average % degree of esterification based on the amount of the two fractions and their % degree of esterification is calculated to 72.3 in good accordance with the value measured on the starting material.

Example 6

The separation was carried out as described in Example 2 except that only 2% IPA was used on the same pectin as in Example 2.

|  | Starting Material | CSP Fraction | NCSP Fraction |
|---|---|---|---|
| degree of esterification % | 71.5 | 65.6 | 77.1 |
| AA % | 83.1 | 85.5 | 84.2 |
| CS | 360 | 1600 | 0.2 |
| % of Fractlons | 100 | 54 | 46 |

The average % degree of esterification based on the amount of the two fractions and their % degree of esterification is calculated to 70.8 in good accordance with the value measured on the starting material.

in the following examples, standardized CSP is used as designation for the pectin according to this invention:

standardized CSP means the calcium sensitive fraction obtained by the separation procedure described above, standardized with sugar or other inert materials to obtain uniform performance.

Example 7

Pate with Reduced Fat Content

Liver pate as produced traditionally contains up to 75% fat. The fat in the formulation is necessary to give the pate the desired form stability and mouth feel; without fat, the pate will be very dry.

it has surprisingly been found that the addition of the CSP makes it possible to prepare a pate with less than 5% fat using the formulation below:

| Ingredients | Full Fat % | Low Fat % |
|---|---|---|
| Liver | 24.00 | 24.00 |
| Pork meat 1 | 12.00 | 12.00 |
| Beef 1 | 20.00 | 20.00 |
| Animal fat | 20.00 | — |
| Water | 17.48 | 40.80 |
| Salt | 1.70 | 1.30 |
| Powdered Onion | 0.42 | — |
| Caseinate | 1.00 | — |
| Ascorbate | 0.05 | 0.05 |
| Wheat flour | 2.50 | — |
| Potato flour | 0.50 | — |
| Flavor | — | 1.00 |
| Phosphate | 0.20 | — |
| Pepper | 0.15 | — |
| Genugel carageenan type MG-11 | — | 0.35 |
| Standardized CSP | — | 1.0 |
| Total | 100.00 | 100.0 |

Process:

1. Liver is ground with salt for 3 minutes.
2. Pork meat is added and ground for 3 minutes.
3. Dry ingredients are added.
4. Water is added and grinding continued for 3 minutes until homogeneous.
5. Finally the beef is ground to desired consistency.
6. The ground meat is poured into cans and autoclaved at 115° C. for 60 minutes.

The pate obtained is judged by specialists in the field to have the same texture as the traditional pates and to be as juicy and tasteful. The composition and process is only an example. Those skilled in the art will be able to modify the composition and the process to suit their special taste preferences and process conditions.

Example 8

Thousand island Dressing with 3% Oil

A thousand island dressing with only 3% oil can be produced with the same organoleptic impression as experienced with the full fat version according to the formulation below.

| Order of Addition | Ingredients | % |
|---|---|---|
| A | Oil | 3.0 |
|  | Standardized CSP | 0.3 |
|  | Whey protein conc./Na-caseinate | 1.0 |
| B | Water | 48.75 |
|  | Egg yolk (past. 1.2% salt) | 5.0 |
|  | Modified starch | 1.0 |
|  | Skimmed milk powder | 4.0 |
|  | Sodium benzoate (20% sol.) | 0.5 |
|  | Potasslum sorbate (20% sol.) | 0.5 |
|  | Sugar | 12.0 |
|  | White pepper | 0.05 |
|  | Paprika | 0.1 |
|  | Garlic powder | 0.1 |
|  | Fat replacer flavor | 0.2 |
| C | Tarragon vinegar (7% acid) | 5.0 |
|  | Vinegar neutral (5%) | 5.0 |
|  | Tomato Paste | 6.5 |
|  | Salt | 1.5 |
|  | Acidified chopped cucumbers | 3.0 |
|  | Pickles | 2.5 |
| Total |  | 100.0 |

Ingredient note:
Whey protein conc.: PSE 73 from Denmark Protein
Skimmed milk Powder: Super Instant
Modified starch: C-top 12616 from Cerestar
Fat replace flavor: Flav-O-Lok 610486 from Tastemaker, Holland Process:
1. Mix ingredients (A).
2. Mix egg yolk+skimmed milk powder into water phase and add preservatives. Blend dry ingredients and mix into water phase. Hydrate for 5 minutes.
3. Mix (A) and (B) and pour into processing equipment (Kuruma or Stephan mixer or equivalent). Mix until homogeneous.
4. Mix ingredients (C) and add slowly. Process until homogeneous, smooth product is achieved.
5. Fill into preferred packaging.

Example 9

Mortadella Sausage was prepared with the following composition:

| Ingredients | % |
| --- | --- |
| Turkey scraps | 45.0 |
| Sodium tripolyphosphate | 0.5 |
| Nitrate salt | 1.6 |
| Genugel type MB-73 | 0.5 |
| Soy Isolate | 1.0 |
| Spices | 0.56 |
| Standardized CSP | 0.9 |
| Ice/water | 46.89 |
| Potato starch | 3.0 |
| Sodium ascorbate | 0.05 |
| Total Ingredients | 100.0 |

Process for preparing Mortadella with Standardized CSP
1. Add 80% of the meat to a bowl chopper and start cutting at low speed.
2. Add phosphate.
3. Add nitrite salt.
4. Add half the water/ice.
5. Add Standardized CSP.
6. Add Genugel® type MB-73, soy isolate and spices.
7. Add remaining water/ice.
8. Add remaining meat quantity.
9. Add potato starch.
10. Cut until desired consistency and texture are achieved.

Smokehouse program
1. Fill the meat into 50 mm smoke permeable casings.
2. Dry the sausages for 30 minutes at 50° C. Smoke for 1 1/2 hours at 55° C. (20% air humidity). Cook at 75° C. until the core temperature reaches 72° C. Cool immediately.

Example 10

A mayonnaise with only 3% oil and the same eating impression as a full fat mayonnaise can be prepared in a very easy way.

| | Ingredients | % |
| --- | --- | --- |
| A | Water | 30.0 |
| | Soy oil | 3.0 |
| | Egg yolk | 4.0 |
| | Modified starch | 3.0 |
| B | Water | 44.15 |
| | Sodium benzoate 20% solids w/v | 0.3 |
| | Potassium sorbate 20% solids w/v | 0.2 |
| C | Standardized CSP | 1.0 |
| | Stabilizer (Hercofood ET 015-1) | 0.6 |
| | Sugar | 5.0 |
| D | Salt (NaCl) | 1.2 |
| E | Vinegar (9.6%) | 5.0 |
| | Mustard | 0.05 |
| | Total | 100.0 |

Process:
1. Add egg yolk, oil and water (A) to Stephan mixer and mix until homogeneous appearance. Add starch and mix again until homogeneous appearance.
2. Add preservative and water (B), mix again.
3. Mix the dry ingredients (C), add to the other ingredients in the mixer, mix for 5 minutes. Let the solution rest for 10 minutes.

The eating quality can be changed from rather thin to heavy by varying the concentration of Standardized CSP. The process is easy—only a blender or a colloid mill is necessary and no homogenizer or other expensive equipment is needed.

Example 11

Low Fat ice Cream

Ice cream normally contains 8–12% milk fat or more to give a rich mouth feel. it has been shown that the same eating quality can be obtained preparing an ice cream with Standardized CSP and only 1.5% fat.

| | Ingredients | % |
| --- | --- | --- |
| A | Milk with 1.5% fat | 78.00 |
| B | Sugar | 15.00 |
| | Skimmed milk powder | 6.60 |
| | Standardized CSP | 0.56 |
| | Emulsifier/stabilizer (Hercofood II 30E-1) | 0.80 |
| | Vanilla flavor | 0.04 |
| | Total | 100.00 |

Process.
1. Weigh out the milk (A).
2. Mix all dry ingredients (B).
3. Disperse the dry powder into the milk.
4. Heat to 80° C.
5. Cool to 5° C.
6. Let the ice-mix ripen for a minimum of 2 hours or until the following day.
7. Freeze the ice-mix, using an ice machine and then in a deep freezer.

The process is simplified compared with traditional ice cream manufacturing procedures. Homogenization is not necessary.

The dry ingredients can be used as a ready blend to mix with semi-skimmed milk by the housewife or ice cream manufacturer.

Example 12

Low Fat Mayonnaise. 20% Oil

| Order of Addition | Ingredients | % |
|---|---|---|
| A | Water | 56.2 |
|   | Egg yolk | 4.0 |
|   | Sodium benzoate (20% sol. w/v) | 0.3 |
|   | Potassium sorbate (20% sol.) | 0.2 |
| B | Soy oil | 20.0 |
|   | Standardized CSP | 0.6 |
|   | Sugar | 5.0 |
|   | VPC 8080 | 2.0 |
|   | Modified starch | 3.0 |
| C | Vinegar estragon (7%) | 7.0 |
|   | Mustard (Dijon) | 0.5 |
|   | Salt (NaCl) | 1.2 |
|   | Total | 100.0 |

Process:

1. Mix water, egg yolk and preservatives.
2. Mix (B) carefully with oil and pour into Stephan mixer.
3. Add (A) to (B) and mix for 5 min.
4. Add (C) and mix for 5 min.
5. Cool to 5° C. (quickly)

Note: May be prepared without egg yolk (with added color, increasing the Standardized CSP.

Example 13

Deep-Frozen Low Fat Sauces

Freeze/thaw stable sauces with Standardized CSP was prepared with the following composition:

| Ingredients | % |
|---|---|
| Water | 83.48 |
| Agar 900-A1 | 1.00 |
| Standardized CSP | 0.40 |
| Starch C*top | 4.00 |
| Skim milk powder | 1.40 |
| Sodium caseinate | 1.50 |
| Salt | 1.00 |
| Pepper | 0.02 |
| Flavor | 0.20 |
| Cream | 7.00 |
| Total | 100.00 |

Process:

1. Mix dry ingredients and add to water and cream using a high speed mixer (Sliverson)
2. Bring to the boil while stirring.
3. Pour into molds and cool to 5° C.
4. Cut into cubes and freeze.

Example 14

Low Fat imitation Sour Cream

| Order of Addition | Ingredients | % |
|---|---|---|
| A | Hardened palm kernel oil (melting point 35° C.) | 3.0 |
|   | Distilled monoglycerides | 0.3 |
|   | Lactic acid ester monoglycerides | 0.45 |
| B | Skimmed milk powder | 4.0 |
|   | Maltodextrine (dextrose equivalent 10–12) | 10.0 |
|   | Standardized CSP | 0.6 |
|   | Genu Carrageenan LRA-50 | 0.8 |
| C | Skimmed milk | 80.85 |
|   | Total Ingredients | 100.00 |

Ingredient note:

Distilled monoglyceride, e.g., Palsgaard 0291.

Lactic acid ester of monoglycerides, e.g., Palsgaard 0404.

Process:

1. Melt fat and emulsifier (A) and heat to 80° C.
2. Mix dry ingredients (B) and dissolve in water phase (C) at 3° C. under continuous agitation. Heat to 80° C.
3. Mix oil phase into water phase under high speed mixing and mix at 75–80° C. for 30 minutes.
4. Homogenize at 150 bars at 75° C.
5. Adjust pH to 4.0 (e.g., with a lactic acid solution).
6. Cool under agitation to approximately 20–30° C.
7. Fill.
8. Ageing at 5° C. for 48 hours.

Example 15

Low Fat Spread with 40% Fat with Standardized CSP

Traditional yellow spreads hold up to 80% fat, but with the use of Standardized CSP it is possible to make a low fat spread of high quality with a fat content of 40% only.

| Order of Addition | Ingredients | % |
|---|---|---|
| A | Coconut oil (Kokoneutrex)[1] | 2.5 |
|   | Hydrogenated palm oil (Palmowar EE42)[2] | 9.3 |
|   | Soya oil (Shogun) | 27.7 |
| B | Distilled monoglyceride (Palsgaard 0291)[3] | 0.6 |
| C | Standardized CSP | 0.8 |
|   | Water | 58.1 |
|   | Salt | 1.0 |
|   | Aroma, color, vitamins, preservatives | optional |
|   | Total Ingredients | 100.0 |

[1] Melting point 26° C.
[2] Melting point 42° C.
[3] Distilled monoglyceride

Process:

1. Heat the oil phase (A) to 43–45° C.
2. Melt the emulsifier (B) with 5 parts of oil/fat from (A) by heating to 60° C and add to the remaining oIl/fat.
3. Heat the water phase (C) to 43–45° C.
4. Prepare a water in oil emulsion by mixing the water phase in the oil phase.
5. Process the emulsion in a tube chiller, working unit and tube chiller (combinator from Schroder, Germany).

Comments:

The Low Fat Spread produced with Standardized CSP according to the above example is more glossy and smoother than the corresponding margarines on the market, and it has an excellent melt down and coherent texture.

The combinator was run under the following conditions:

| Inlet temperature | 43–45° C. |
|---|---|
| Outlet temperature CC1 (tube chiller No. 1) | 23–25° C. |
| A1 (working unit) | 35–40° C. |
| CC2 (tube chiller No. 2) | 15–25° C. | rpm of CCA: 800; A1: 1400, CC2: 750

Example 16

Low Fat Spread with 20–25% Fat With Standardized CSP

Traditional yellow spreads hold up to 40–80% fat, but with the use of Standardized CSP it is possible to make a low fat spread of high quality with a fat content of 20–25% only. Which one of the two below recipes to be chosen depends on the preferred emulsifier system.

| Order of Addition | Ingredients | 20% fat | 25% % |
|---|---|---|---|
| A | Hydrogenated palm oil (Palmowar EE42)[1] | 6.6 | 8.3 |
|   | Soya oil (Shogun) | 13.4 | 16.2 |
| B | Emulsifier |   |   |
|   | (Palsgaard 0291)[2] | 0.7 | — |
|   | (Palsgaard 4110)[3] | 0.2 | — |
|   | (Palsgaard 0094)[2] | — | 1.0 |
| C | Standardized CSP | 0.8 | 0.8 |
|   | Water | 77.3 | 72.7 |
|   | Salt | 1.0 | 1.0 |
|   | Aroma, color, vitamins, preservatives | optional | optional |
|   | Total ingredients | 100.0 | 100.0 |

[1]Melting point 42° C.
[2]Distilled monoglyceride
[3]Polyglycerol polyricinoleate Process:

1. Heat the oil phase (A) to 43–45° C.
2. Melt the emulsifier (B) with 5 parts of oil/fat from (A) by heating to 60° C. and add to the remaining oil/fat.
3. Heat the water phase (C) to 43–45° C.
4. Prepare a water in oil emulsion by mixing the water phase in the oil phase.
5. Process the emulsion in a tube chiller, working unit and tube chiller (combinator from Schroder, Germany).

Comments:

The Low Fat Spread produced with Standardized CSP according to the above example is more glossy and smoother than the corresponding margarines on the market, and it has an excellent melt down and coherent texture.

The combinator was run under the following conditions:

| Inlet temperature | 43–45° C. |
|---|---|
| Outlet temperature CC1 (tube chiller No. 1) | 23–25° C. |
| A1 (worklng unit) | 35–40° C. |
| CC2 (tube chiller No. 2) | 15–25° C. | rpm of CCA: 800; A1: 1400, CC2: 750

Example 17

Skimmed Milk with Improved Mouthfeel

| Ingredients | % |
|---|---|
| Standardized CSP | 0.30 |
| Stabilizer GENULACTA carrageenan type LK-60 | 0.03 |
| Flavor* | 0.05 |
| Skimmed milk | 99.62 |
| Total | 100.0 |

Process:

1. Dry mix all the ingredients.
2. Disperse the dry mix into the cold milk by use of a high speed mixer.
3. Homogenize at 200 bar, 1 step.
4. Pasteurize at 85° C.
5. Fill at 18–20° C.
6. Store at 5° C.

Example 18

The water absorption of the calcium sensitive fraction in accordance with this invention was determined.

The measurements were carried out with water containing 1% NaCl according to the method described under Analytical Procedures.

By water absorption is understood the ability of the pectin sample to take up water, when immersed in distilled water or 1% NaCl solution made with distilled water.

The results obtained with a number of samples are reported in the table below.

| Sample Designation | Tea Bag, 1% NaCl Abstract, g/g |
|---|---|
| 92-PEG-35A | 20.4 |
| 92-PEG-48-1a | 22.0 |
| 92-PEG-54-1 | 58.7 |
| 93-PEG-4A | 55.0 |
| 93-PEG-16A.1 | 41.6 |
| 93-PEG-16A.2 | 20.7 |
| 93-PEG-7A.1 | 46.8 |
| 93-PEG-7A.2 | 22.6 |

-continued

| Sample Designation | Tea Bag, 1% NaCl Abstract, g/g |
|---|---|
| 93-PEG-10A.1 | 37.2 |
| 93-PEG-10A.2 | 33.3 |
| 93-PEG-23A.1 | 32.3 |
| 93-PEG-23A.2 | 35.1 |

What is claimed:

1. A process comprising treating a solution, gel or suspension of pectin starting material having a degree of esterification greater than about 60% with a cation-containing preparation to obtain at least a first fraction having a higher degree of calcium sensitivity and a second fraction having a lower degree of calcium sensitivity than said pectin starting material wherein the cation-containing preparation comprises a cation that is a metal ion derived from salts selected from the group consisting of alkaline earth metal salts, alkali metal salts, transition metal salts, and mixtures thereof.

2. The process of claim 1 wherein the cation-containing preparation contains a di- or trivalent cation and optionally at least one water miscible solvent.

3. The process of claim 2 wherein the cation is calcium.

4. The process of claim 2 further comprising separating said first and second fractions into gel and liquid fractions, respectively.

5. The process of claim 2 further comprising washing said gel fraction with said cation-containing preparation.

6. The process of claim 2 further comprising dehydrating, drying and milling said fractions.

7. The process of claim 1 which is continuous.

8. The process of claim 5 wherein the at least first fraction has a calcium sensitivity of at least 10% higher than the starting material.

9. The process of claim 5 wherein the at least first fraction has a calcium sensitivity of at least 25% higher than the starting material.

10. The process of claim 5 wherein the at least first fraction has a calcium sensitivity of at least 50% higher than the starting material.

11. The process of claim 5 wherein the at least first fraction has a calcium sensitivity of at least 100% higher than the starting material.

12. The process of claim 1 wherein the at least first fraction has a degree of esterification lower than the degree of esterification of the starting material and the second fraction has a degree of esterification higher than the degree of esterification of the starting material.

13. The process of claim 12 wherein the at least first fraction has a degree of esterification of at least 1% lower than the degree of esterification of the starting material.

14. The process of claim 12 wherein the at least first fraction has a degree of esterification of at least 3% lower than the degree of esterification of the starting material.

15. The process of claim 12 wherein the at least first fraction has a degree of esterification of at least 5% lower than the degree of esterification of the starting material.

16. The process of claim 12 wherein the second fraction has a degree of esterification of at least 1% higher than the degree of esterification starting material.

17. The process of claim 12 wherein the second fraction has a degree of esterification of at least 3% higher than the degree of esterification starting of the material.

18. The process of claim 12 wherein the second fraction has a degree of esterification of at least 7% higher than the degree of esterification of the starting material.

19. The process of claim 1 wherein the cation is selected from the group consisting of calcium, magnesium, iron, zinc, potassium, sodium, aluminum, manganese, and mixtures thereof.

* * * * *